United States Patent
Gai et al.

(10) Patent No.: US 12,064,458 B2
(45) Date of Patent: Aug. 20, 2024

(54) **USE OF *RHODOCOCCUS RUBER* PRODUCT IN TREATING THERMAL INJURY**

(71) Applicant: LIAONING GREATEST BIO-PHARMACEUTICAL CO. LTD., Benxi (CN)

(72) Inventors: Bo Gai, Benxi (CN); Chunyan Dou, Benxi (CN); Yi Zhang, Benxi (CN); Guoying Zhang, Benxi (CN)

(73) Assignee: Liaoning Greatest Bio-Pharmaceutical Co., Ltd., Benxi (CN)

( * ) Notice: Subject to any disclaimer, the term of this patent is extended or adjusted under 35 U.S.C. 154(b) by 66 days.

(21) Appl. No.: 17/604,364

(22) PCT Filed: Apr. 23, 2020

(86) PCT No.: PCT/CN2020/086353
§ 371 (c)(1),
(2) Date: Oct. 15, 2021

(87) PCT Pub. No.: WO2020/216281
PCT Pub. Date: Oct. 29, 2020

(65) Prior Publication Data
US 2022/0175852 A1 Jun. 9, 2022

(30) Foreign Application Priority Data
Apr. 24, 2019 (CN) .......................... 201910333119.3

(51) Int. Cl.
A61K 35/74 (2015.01)

(52) U.S. Cl.
CPC .................................... *A61K 35/74* (2013.01)

(58) Field of Classification Search
CPC .................................................... A61K 35/74
See application file for complete search history.

(56) References Cited

U.S. PATENT DOCUMENTS

| | | | | |
|---|---|---|---|---|
| 2022/0193148 A1* | 6/2022 | Gai | .......................... | C12N 1/20 |
| 2022/0241348 A1* | 8/2022 | Gai | .......................... | C12N 1/205 |

FOREIGN PATENT DOCUMENTS

| | | | | |
|---|---|---|---|---|
| CN | 1094288 | A | 11/1994 | |
| CN | 2002-179575 | A | 6/2002 | |
| CN | 1519312 | A | 8/2004 | |
| CN | 101033454 | A | 9/2007 | |
| CN | 101209267 | A | 7/2008 | |
| CN | 101580808 | A | 11/2009 | |
| CN | 101619299 | A | 1/2010 | |
| CN | 102250796 | A | 11/2011 | |
| CN | 102604875 | A | 7/2012 | |
| CN | 103160491 | A | 6/2013 | |
| CN | 103509833 | A | 1/2014 | |
| CN | 103627653 | A | 3/2014 | |
| CN | 104830738 | A | 8/2015 | |
| CN | 105820982 | A | 8/2016 | |
| CN | 10643446 | A | 2/2017 | |
| CN | 106591168 | A | 4/2017 | |
| CN | 106591172 | A | 4/2017 | |
| CN | 107151635 | A | 9/2017 | |
| CN | 107233362 | A | 10/2017 | |
| CN | 108130288 | A | 6/2018 | |
| CN | 108862590 | A | 11/2018 | |
| CN | 112218647 | B | 7/2023 | |
| JP | 2003-052362 | A | 2/2003 | |
| JP | 2003-052366 | A | 2/2003 | |
| WO | WO-2007132790 | A1 * | 11/2007 | ............ A61K 35/74 |
| WO | 2018/208530 | A1 | 11/2018 | |

OTHER PUBLICATIONS

Wang, Yi et al. "Nocardia Rubra Cell Wall Skeleton Accelerates Cutaneous Wound Healing by Enhancing Macrophage Activation and Angiogenesis." Journal of international medical research 46.6 (2018): 2398-2409. Web. (Year: 2018).*
"Rhodococcus ruber—microbewiki." (2020) Retrieved from web: https://microbewiki.kenyon.edu/index.php/Rhodococcus_ruber (Year: 2020).*
Zhao, Jingling et al. "Granulocyte/macrophage Colony-Stimulating Factor Influences Angiogenesis by Regulating the Coordinated Expression of VEGF and the Ang/Tie System." PloS one 9.3 (2014): e92691-. Web. (Year: 2014).*
Kuyukina MS, Ivshina IB, Baeva TA, Kochina OA, Gein SV, Chereshnev VA. Trehalolipid biosurfactants from nonpathogenic Rhodococcus actinobacteria with diverse immunomodulatory activities. N Biotechnol. Dec. 25, 2015;32(6):559-68. doi: 10.1016/j.nbt.2015.03.006. Epub Mar. 18, 2015. PMID: 25796474. (Year: 2015).*
Machine English translation of WO2007132790A1 obtained from Espacenet.com. (Year: 2023).*
Alberta—Second-Degree Burn retrieved from https://myhealth.alberta.ca/Health/Pages/conditions.aspx?hwid=tp12218#:~:text=A%20deep%20second%2Ddegree%20burn,may%20be%20painful%20with%20pressure. (Year: 2023).*

(Continued)

*Primary Examiner* — Louise W Humphrey
*Assistant Examiner* — John Paul Selwanes
(74) *Attorney, Agent, or Firm* — Rodney J. Fuller; BOOTH UDALL FULLER, PLC

(57) ABSTRACT

A use of a cell wall or a cell wall skeleton of *Rhodococcus ruber* in preparing a drug for treating a thermal injury. The thermal injury comprises a burn, a scald and a chemical burn. Applying the *Rhodococcus ruber* product to a subject has a good therapeutic effect on a thermal injury and has no side effects.

19 Claims, 2 Drawing Sheets
Specification includes a Sequence Listing.

(56) References Cited

OTHER PUBLICATIONS

Hua, Gougen et al., "The taxonomy and application of Rhodococcus", Microbiology China, 30(4):107-111, English abstract only (2003).

You, Xiaona et al., "Study on the identification of the production strain about N-CWS", Chinese Journal of Bioprocess Engineering, 11(4):55-58, English abstract only (Jul. 2013).

Foster, Kevin, "Clinical Guidelines in the Management of Burn Injury: A Review and Recommendations from the Organization and Delivery of Burn Care Committee", Journal of Burn Care & Research, 35(4):271-283 (Jul.-Aug. 2014).

\* cited by examiner

```
GGTTAAGGCCACCGGCTTCGGGTGTTACCGACTTTCATGACGTGACGGGCGGTGTGTACAAGGCCCGGGAACGTATTCACCGCA
GCGTTGCTGATCGCGATTACTAGCGACTCCGACTTCACGGGGTCGAGTTGCAGACCCGATCGAACTGAGACGGCTTTAA
GGGATTCGCTCCACCTCGCGGTATCGCACCCTCTGTACCGGCCATTGTAAGCCTGGAACATAAGGGGCATGA
TGACTTGACGTCGTCCCACCTTCCTCCGAGTTGACCCGCGGCAGTCTCTGCAGTCCCCATTACGTGCAACACAG
GACAAGGGTTGCCGTTGCGGGACTTAACCAACATCTCACGACACGAGCTGACGACACCATGCACCACCGTACCGA
CCACAAGGGAAACCCCATCTCTGGGGCGGTATGTCAAGCCCAGGTAAGGTTCTTCGCGTTGCATCGAATTAATCCA
CATGCTCCGCCGCCTGTGCGGGCCCCCGTCAATTCCTTTGAGTTTTAGCCTTGGCCGTACTCCCCAGGCGGGGCGCTTAAT
GCGTTAGCTACGGCACGGATCCGTGAAGGAAACCCACACTTAGCTGCCAGTTACGGCGTTACGGCGTGGACTACCAGGGTATCTAA
TCCTGTTCGCTACCCATGCTTTCGCTCTACACCGGAATTCCAGTCTCCCTGCAGTACTCAAGTCGCCCGAGACCGCCTTCGCCACCGGTGTTCCTCCTGATA
TCTGCGCATTTCACCGCTACACCTGGAATTCCAGTCTCCCTGCAGTACTCAAGTCGCCCGTATCGCCTGCAAGCCTGGCAGT
TGAGCTGCGGGTTTCACAGAGACGACGACAAACCGCCTACGAGCTCTTTACGCCCAGTAATTCCGACAACCTCGCACCT
ACGTATTACCGCGGCTGCTGGCACGGAGTTAGCCGGTGCTTCTTCTGTAGTCGCCGGTTCGCCGCCGTCCGGTTCCGGTACTGAAAG
AGGTTTACAACCCGAAGGCCGTCATCCTTCACGGGGCCCCTCAGTGTGGCCGGTGTGCCTCAGCCTCCACCTGTCAATATCCCCACTGCT
GCCTCCCGTAGGAGTCTGGGCCGTGTCCAGTCGCATGATAGGCCGGGGCCGGGGCTACCCGTCCCCTTGGT
GGGCCGTTACCCACCAACAAGCTGATTAGGCCTTATCCCGAAGCCGCAGGATCACCACCCGTGTTACTCACCGTTCG
AGGTCCTATCCGGTATTAGACCCAGTTTCCCAGGCTTATCCCGAAGTGCAGGCAGATCACCACCGTGTTACTCACCGTTCG
CCACTAATCCACCAGCAAGCTGGTTCATGCTTCGAC
```

Figure 2

USE OF *RHODOCOCCUS RUBER* PRODUCT IN TREATING THERMAL INJURY

CROSS REFERENCE TO RELATED APPLICATIONS

This application is the U.S. National Stage of International Application No. PCT/CN2020/086353 filed on Apr. 23, 2020, which claims the priority of the patent application number CN201910333119.3 filed on Apr. 25, 2019, the contents of each of which are incorporated herein by reference in their entireties.

BIOLOGICAL DEPOSIT OF *RHODOCOCCUS RUBER* ACCESSION NO. 17431

A Biological Deposit of *Rhodococcus Ruber* Accession No. 17431 was made at the China General Microbiological Culture Collection Center (CGMCC) (Yard No. 1(3) West Beichen Road, Chaoyang District, Beijing, Institute of Microbiology, Chinese Academy of Sciences; postal code: 100101), on Mar. 22, 2019, under the provisions of the Budapest Treaty, and assigned by the International Depositary Authority the accession number 17431. Upon issuance of a patent, all restrictions upon the Deposit will be irrevocably removed, and the Deposit is intended to meet the requirements of 37 CFR §§ 1.801-1.809. The Deposit will be maintained in the depository for a period of 30 years, or 5 years after the last request, or for the effective, enforceable life of the patent, whichever is longer, and will be replaced, if necessary, during that period; and the requirements of 37 CFR §§ 1.801-1.809 are met.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 2,077 byte ASCII (text) file named "SeqList" created on Apr. 23, 2020.

TECHNICAL FIELD OF THE INVENTION

The present disclosure relates to the fields of medicine, microbiology and biopharmacy. Specifically, it relates to *Rhodococcus ruber* and cell wall components, formulations, pharmaceutical compositions and preparation methods thereof, as well as use of *Rhodococcus ruber* cell wall components in the preparation of a medicament/medical device for the treatment of thermal injury.

BACKGROUND OF THE INVENTION

*Rhodococcus ruber* is a gram-positive bacterium. Generally, its colony is orange-yellow or orange-red in color, and round in shape; the size of the colony is about 1 mm to 2 mm; the cell morphology is spherical or short rod-shaped; it can form primary branched mycelium; and it has no flagella. *Rhodococcus ruber* is aerobic and chemically heterotrophic.

At present, researchers have performed whole gene sequencing for *Rhodococcus ruber*. For example, Fan Xin et al. sequenced the whole genome of *Rhodococcus ruber* SD3 strain and performed bioinformatic analysis. The whole genome length of the SD3 strain is about 5.37 Mb, the GC content is about 70.63%, and the GenBank accession number is CP029146 (Fan Xin, Whole-genome sequencing and expression analysis of heat shocking protein DnaK from *Rhodococcus ruber* SD3, Genomics and Applied Biology, January 2019).

The *Rhodococcus* genus can adapt to a variety of living environments due to its strong tolerance to organic substances and its wide degradation spectrum. Therefore, *Rhodococcus* is widely used in the fields of pollution remediation, organic compound degradation, sewage treatment, etc. At present, the main application field of *Rhodococcus ruber* lies in environmental management, see CN108862590A, CN107151635A, CN102250796A, CN1519312A, CN103627653A, CN101033454A, CN108130288A, CN104830738A, CN101619299A, CN103509833A, CN106434466A, CN101580808A, CN102604875A, CN103160491A, CN106591168A, CN106591172A and CN105820982A.

CN109576180A discloses a bacterium RDC-01 screened from the red soil in the suburbs near Panyu District, Guangzhou. After 16S rRNA gene sequence analysis and cultivation characteristics identification, the strain was identified as *Rhodococcus ruber*. After inactivation, the bacterium as an immune adjuvant was added to an inactivated vaccine for animals, and it was found to be able to promote the production of antibodies in animals.

In the field of trauma surgery, the anti-infective therapeutic principle is mostly used for thermal injuries, especially the wounds caused by burns or scalds. The healing of skin thermal injury is a complex biological process, which is affected by a variety of cytokines, vascular endothelial cells, fibroblasts, keratinocytes and other various factors.

However, the application of *Rhodococcus ruber* in the field of medicine used for human has not yet been reported.

SUMMARY OF THE INVENTION

According to some embodiments of the present disclosure, provided is an isolated *Rhodococcus ruber*.

According to some particular embodiments of the present disclosure, provided is a *Rhodococcus ruber*, which was deposited at China General Microbiological Culture Collection Center (CGMCC) on Mar. 22, 2019 (Address: Institute of Microbiology, Chinese Academy of Sciences, Yard No. 1(3) West Beichen Road, Chaoyang District, Beijing China, postal code: 100101) under deposit number CGMCC No. 17431. The deposit meets the requirements of the Budapest Treaty on the International Recognition of the Deposit of Microorganisms for the Purposes of Patent Procedure.

According to some embodiments of the present disclosure, a *Rhodococcus ruber* and derivative products thereof are provided. The derivative products are derived from *Rhodococcus ruber* and comprise the components of *Rhodococcus ruber* (such as proteins, nucleic acids, lipids, cell walls and components thereof, carbohydrates or metabolites).

In particular embodiments, provided is an isolated *Rhodococcus ruber* cell wall.

In particular embodiments, provided is an isolated *Rhodococcus ruber* cell wall, the *Rhodococcus ruber* referring to the strain under the deposit number CGMCC No. 17431.

In particular embodiments, provided is an isolated *Rhodococcus ruber* cell wall skeleton.

In particular embodiments, provided is an isolated *Rhodococcus ruber* cell wall skeleton, the *Rhodococcus ruber* referring to the strain under the deposit number CGMCC No. 17431.

According to some embodiments of the present disclosure, provided is a pharmaceutical composition, which comprises *Rhodococcus ruber* cell wall or *Rhodococcus ruber* cell wall skeleton according to the present disclosure.

According to some embodiments of the present disclosure, provided is a product derived from *Rhodococcus ruber*, which comprises a product obtained by disruption of *Rhodococcus ruber*.

According to some other embodiments of the present disclosure, provided is a product derived from *Rhodococcus ruber*, which comprises a product obtained by disruption and purification (removing lipids, nucleic acids and proteins) of *Rhodococcus ruber*.

According to some other embodiments of the present disclosure, provided is a product derived from *Rhodococcus ruber*, which comprises *Rhodococcus ruber* cell wall.

According to some other embodiments of the present disclosure, provided is a product derived from *Rhodococcus ruber*, which comprises *Rhodococcus ruber* cell wall skeleton.

According to some embodiments of the present disclosure, provided is a pharmaceutical composition or a medical device, which comprises a product obtained by disruption of *Rhodococcus ruber*.

According to some other embodiments of the present disclosure, provided is a pharmaceutical composition or a medical device, which comprises a product obtained by disruption and purification (removing lipids, and/or nucleic acids, and/or proteins) of *Rhodococcus ruber*.

According to some other embodiments of the present disclosure, provided is a pharmaceutical composition or a medical device, which comprises *Rhodococcus ruber* cell wall.

According to some other embodiments of the present disclosure, provided is a pharmaceutical composition or a medical device, which comprises *Rhodococcus ruber* cell wall skeleton.

According to some other embodiments of the present disclosure, provided is a pharmaceutical composition or a medical device, which comprises the product derived from *Rhodococcus ruber* as described above.

In particular embodiments, the pharmaceutical composition further comprises a pharmaceutically acceptable excipient.

In some embodiments of the pharmaceutical composition, the product derived from *Rhodococcus ruber* is 1 part by weight, and the pharmaceutically acceptable excipient is 100 to 1000 parts by weight (100, 200, 300, 400, 500, 600, 700, 800, 900, 1000), preferably 200 to 500 parts by weight, more preferably 200 to 300 parts by weight (for example, 200, 210, 220, 230, 240, 250, 260, 270, 280, 290, 300 and any value within the range between any two numbers above).

In some other embodiments of the pharmaceutical composition, the *Rhodococcus ruber* cell wall is 1 part by weight, and the pharmaceutically acceptable excipient is 100 to 1000 parts by weight (100, 200, 300, 400, 500, 600, 700, 800, 900, 1000), preferably 200 to 500 parts by weight, more preferably 200 to 300 parts by weight (for example, 200, 210, 220, 230, 240, 250, 260, 270, 280, 290, 300 and any value within the range between any two numbers above).

In still other embodiments of the pharmaceutical composition, the *Rhodococcus ruber* cell wall skeleton is 1 part by weight, and the pharmaceutically acceptable excipient is 100 to 1000 parts by weight (100, 200, 300, 400, 500, 600, 700, 800, 900, 1000), preferably 200 to 500 parts by weight, more preferably 200 to 300 parts by weight (for example, 200, 210, 220, 230, 240, 250, 260, 270, 280, 290, 300 and any value within the range between any two numbers above).

In some embodiments, the pharmaceutical composition can be prepared as a liquid (liquid formulation).

In some other embodiments, the pharmaceutical composition can be prepared as a solid (powder formulation or lyophilized formulation).

The skilled person understands that, for the pharmaceutical composition of the present disclosure, the liquid formulation and the powder formulation (or lyophilized formulation) can be converted into each other, and the difference lies only in the water content. A powder formulation (or lyophilized formulation) is obtained by removing most or all of the water from the liquid formulation. A liquid formulation is obtained by dissolving (or reconstituting) the powder formulation (or lyophilized formulation).

In some embodiments, the medicament or pharmaceutical composition is formulated into a dosage form selected from the group consisting of: ointment, cream, emulsion, suspension, paste, gel, lotion, tincture, oil, tablet, aerosol, spray, liniment, powder and suppository; wherein, the ointment is selected from the group consisting of: soft ointment, plaster and cream.

In some embodiments, the dosage form is a form suitable for application onto the lesion. For example, spray, ointment, lotion, dressing and patch.

In some embodiments, the pharmaceutically acceptable excipient relates to, but is not limited to: filler, stabilizer, flavoring agent, disintegrant, binder and lubricant.

In some embodiments, the pharmaceutically acceptable excipient is for example but not limited to: dextran, lactose, microcrystalline cellulose, trehalose, glycine, xylitol, sodium carboxymethyl cellulose, erythritol, gelatin, magnesium stearate, propellant, humectant, solvent, solubilizer, emulsifier, antioxidant, pH regulator and preservative.

In some embodiments, non-limiting examples of the pharmaceutically acceptable excipient also include: white vaseline, carbomer, hydroxypropyl methylcellulose, methyl cellulose, sodium hydroxymethyl cellulose, chitosan, sucralfate chitosan, polyvinylpyrrolidone, polyvinyl alcohol, sodium hyaluronate, dimethyl ether, tetrafluoroethane, hydrofluoroalkane, glycerin, propylene glycol, deionized water, water for injection, distilled water, ethanol, hexadecanol, octadecanol, p-aminobenzoic acid, acetamide, isopropanol, Tween, polyoxyethyl hydrogenated castor oil, stearic acid, glyceryl monostearate, triglycerol monostearate, sucrose fatty acid ester, sucrose ester, sucrose acetate isobutyrate, sorbitan tristearate, isopropyl myristate, cholesterol, squalene, squalane, n-butanol, ethylene glycol, ethanol, propylene glycol, polyglycerol ester, sulfite, cysteine, di-tert-butyl hydroxytoluene, potassium sorbate, phosphate buffer solution, triethanolamine, sodium hydroxide, ethylenediamine, laurylamine, sodium bicarbonate, hydrochloric acid, nipagins, thimerosal, chlorocresol, trichlorobutanol, benzoic acid and sodium salt thereof.

According to some embodiments of the present disclosure, provided is a method for the preparation of products derived from *Rhodococcus ruber*, which comprises or consists of the following steps:

1) providing a *Rhodococcus ruber*;
2) optionally, culturing the *Rhodococcus ruber*;
3) optionally, collecting the cultured *Rhodococcus ruber*;
4) disrupting the cultured *Rhodococcus ruber* to obtain a disrupted product;
5.1) optionally, removing lipids from the disrupted product;
5.2) optionally, removing nucleic acids from the disrupted product;

5.3) optionally, removing proteins from the disrupted product;
5.4) obtaining a purified product;
6) optionally, removing water from the purified product, preferably removing water from the purified product by lyophilization;
7) optionally, performing aliquoting;
8) harvesting the product derived from *Rhodococcus ruber*;
wherein, steps 5.1), 5.2) and 5.3) are interchangeable in order or performed in parallel; step 6) and step 7) are interchangeable in order.

Optionally, where necessary, step 5) can further comprise a step of removing the cell membranes (for example, by using a non-ionic surfactant).

The Culture of *Rhodococcus ruber* is not limited to particular culture medium and culture parameters, and the skilled person can use well-known and appropriate methods for cultivation, and can use petri dishes, culture flasks and fermenters according to the preparation scale.

For the disruption of *Rhodococcus ruber*, the purpose is to remove the substances present inside the cells, therefore ultra-sonication, lysozyme and other technologies can be used. The skilled person understands that any known or future method suitable for disrupting gram-positive bacteria is suitable for the technical solution of the present disclosure.

The skilled person has the ability to adjust the particular parameters and equipment for culture, disruption, separation, collection, removal of impurity, and aliquoting according to the subsequent application (for example external application) of the active ingredient (the cell wall and components thereof), so as to avoid introducing factors that affect the subsequent application into the preparation steps.

In some embodiments, for example an organic solvent is used to remove lipids from the disrupted product. In some embodiments, for example a nuclease is used to remove DNA and RNA from the disrupted product. In some embodiments, for example a hydrolase is used to degrade proteins in the disrupted product. In some embodiments, for example a surfactant is used to remove cell membranes from the disrupted product.

In some embodiments, the average particle size of disruption is 10 nm to 1000 nm; mention may be made of 10, 20, 30, 40, 50, 60, 70, 80, 90, 100, 110, 120, 130, 140, 150, 160, 170, 180, 190 nm±10 nm, and the ranges between any two of the above values. There are many methods for measuring the particle size (Hu Songqing et al., Modern technology of particle size measurement, Modern Chemical Industry, 2002, 22:1).

In some particular embodiments, the average particle size of disruption is 10 nm to 800 nm.

In some other particular embodiments, the average particle size of disruption is 10 nm to 500 nm.

In some particular embodiments, the aliquoting refers to aliquoting into containers or onto solid supports. The container is selected from the group consisting of: vial, tube, package, bag, plate, ampoule, injection device, aluminum-plastic packaging, dressing and capsule.

For example, in particular embodiments, the aliquoting refers to aliquoting into vials/ampoules. Solvent is added to the vial/ampule just before use.

According to some embodiments of the present disclosure, provided is a product derived from *Rhodococcus ruber*, which is obtained by the preparation method of the present disclosure.

According to some embodiments of the present disclosure, provided is a pharmaceutical composition or a medical device, which comprises a product derived from *Rhodococcus ruber* obtained by the preparation method of the present disclosure.

According to some embodiments of the present disclosure, provided is an isolated *Rhodococcus ruber* cell wall, which is used for the treatment of thermal injury.

According to some embodiments of the present disclosure, provided is a product derived from *Rhodococcus ruber*, which is used for the treatment of thermal injury.

According to some embodiments of the present disclosure, provided is a pharmaceutical composition or a medical device, which is used for the treatment of thermal injury.

According to some embodiments of the present disclosure, provided is use of the *Rhodococcus ruber* cell wall according to the present disclosure in the treatment of thermal injury.

According to some embodiments of the present application, provided is use of the *Rhodococcus ruber* cell wall of the present disclosure in the preparation of a medicament/medical device for the treatment of thermal injury.

According to some embodiments of the present disclosure, provided is use of the product derived from *Rhodococcus ruber* according to the present disclosure in the treatment of thermal injury; also provided is use of the product derived from *Rhodococcus ruber* of the present disclosure in the preparation of a medicament/medical device for the treatment of thermal injury.

According to some embodiments of the present disclosure, provided is use of the pharmaceutical composition according to the present disclosure in the treatment of thermal injury.

In some embodiments, the thermal injury can be caused by a factor selected from the group consisting of: burn, scald and chemical burn.

In some embodiments, the thermal injury can involve tissue(s) selected from the group consisting of: epidermis, dermis, mucosa and subcutaneous tissue.

In some embodiments, the thermal injury is a first, second (deep, superficial), or third degree injury.

In this application, the severity of thermal injury is divided into: first degree, superficial second degree, deep second degree and third degree, according to the Rule of three degrees with four levels:

First degree: only the epidermis is injured, with local redness and swelling;
Second degree: deep into the dermis, with local blisters;
  Superficial second degree: only the epidermal germinal layer and dermal papillary layer are injured;
  Deep second degree: the dermis is injured, with remaining skin appendages;
Third degree: all layers of the skin are injured, even reaching subcutaneous tissue, and deep into muscles, bones, etc.

In particular embodiments, the product derived from *Rhodococcus ruber*/*Rhodococcus ruber* cell wall/pharmaceutical composition according to the present application is especially used for the treatment of deep second degree thermal injury.

According to some embodiments of the present disclosure, provided is use of any one selected from the following in the preparation of a medicament (or medical device):
  the *Rhodococcus ruber* according to the present disclosure,
  the isolated *Rhodococcus ruber* cell wall according to the present disclosure, the product derived from *Rhodococcus ruber* according to the present disclosure, the pharmaceutical composition according to the present disclosure.

In some particular embodiments, the medicament is used for the treatment of thermal injury.

In some particular embodiments, the medical device (such as dressing, patch, bandage, film, patch, etc.) is used for the treatment of thermal injury.

According to some embodiments of the present disclosure, also provided is a method for the treatment of thermal injury, including exposing a subject (lesion) to a therapeutically effective amount of any one selected from of the following:

the isolated *Rhodococcus ruber* cell wall according to the present disclosure, the product derived from *Rhodococcus ruber* according to the present disclosure, the pharmaceutical composition according to the present disclosure, the medical device according to the present disclosure.

In some particular embodiments, the medicament (or the medical device) is administered to a lesion at different doses, according to the area and severity of the lesion. For example, but not limited to:

applying a medicament comprising *Rhodococcus ruber* cell wall skeleton; or covering the lesion with a patch (or film or gauze) impregnated with *Rhodococcus ruber* cell wall skeleton;

directly applying the lyophilized powder comprising *Rhodococcus ruber* cell wall skeleton to the lesion; or applying an ointment/cream comprising *Rhodococcus ruber* cell wall skeleton to the lesion.

Pharmaceutical solution, ointment and powder can be applied alternately onto the lesion.

Regarding the dose of each administration, different doses are used depending on the area size and severity of the patient's lesions, usually from 5 µg to 800 µg/unit dose/each administration, preferably 10 µg to 600 µg/unit dose/each administration.

In some particular embodiments, the period of contact lasts for 2 days to 4 months or longer. Specifically, for example 2, 4, 6, 8, 10, 15, 20, 25, 30, 35, 40, 45, 50, 55, 60 days; as another example, 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks or longer can be mentioned. In particular embodiments, the active ingredient is administered to a subject for 3 to 5 weeks.

In some embodiments, the administration is performed at a frequency selected from the group consisting of: administering 1 to 3 times a day, 1 to 6 times every two days, 1 to 9 times every three days, 1 to 14 times a week, 1 to 60 times a month. In some embodiments, the active ingredient is administered twice a day, or once a day, or once every two days.

Regarding the amount of each administration, different doses are applied depending on the specific conditions of the subject, usually 1 µg to 1000 µg/unit dose/each administration; specifically, for example 1, 5, 10, 15, 20, 25, 30, 35, 40, 45, 50, 55, 60, 65, 70, 75, 80, 85, 90, 95, 100, 110, 120, 130, 140, 150, 160, 170, 180, 190, 200 µg/unit dose/each administration, and the range between any two of the above values.

In some particular embodiments, the product derived from *Rhodococcus ruber*, the pharmaceutical composition or the medical device of the present disclosure is in contact with the lesion site for a few minutes to a few hours, for example 30 minutes to 24 hours.

In some particular embodiments, the product derived from *Rhodococcus ruber*, the pharmaceutical composition or the medical device of the present disclosure is in contact with the lesion site at a frequency of: once a day, or twice a day, or once every two days.

In some embodiments, the aforementioned treatment methods are applicable to any animal with skin/mucosal structure, including but not limited to: human, non-human primate, suidae, bovine, equine, ovine, canidae, feline, murine and lepidae.

In some particular embodiments, the subject is an animal other than human, for example farm animal, pet, working animal, ornamental animal and production animal.

In particular embodiments, the subject is a human.

In some particular embodiments, the only therapeutic (or prophylactic) active ingredient in the medicament or the medical device is a product derived from *Rhodococcus ruber*, notably comprising components of *Rhodococcus ruber* (such as proteins, nucleic acids, lipids, cell walls and components thereof, carbohydrates or metabolites), specifically, products comprising *Rhodococcus ruber* cell wall (more preferably *Rhodococcus ruber* cell wall skeleton or components thereof).

DESCRIPTION OF THE DRAWINGS

FIG. 2: The identification results of 16S rRNA.

DETAILED DESCRIPTION OF THE EMBODIMENTS

Figure 1:
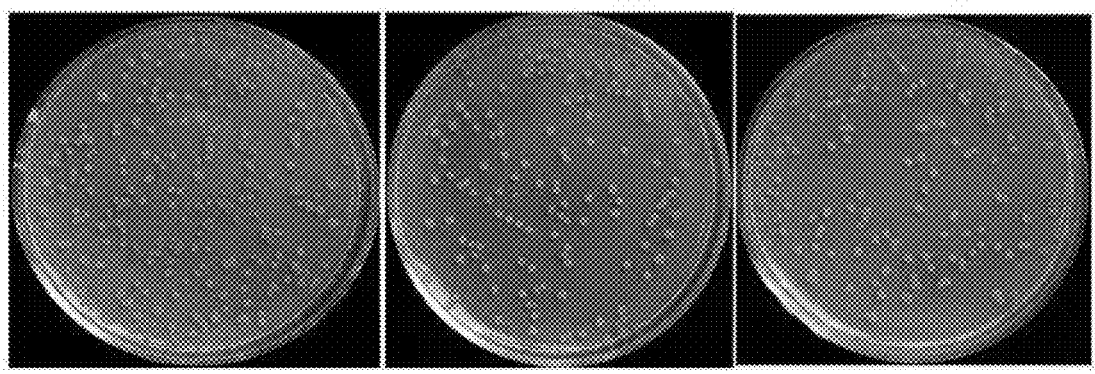
FIG. 1: The colony morphology of *Rhodococcus ruber*.

"Isolation" refers to the separation of the *Rhodococcus ruber* of the present disclosure from its original growth environment.

The skilled person knows that the cell wall structures of gram-positive bacteria and gram-negative bacteria are different. Specifically, the cell wall of gram-positive bacteria is thicker (usually 20 nm to 80 nm), comprising about 90% peptidoglycan and about 10% teichoic acid (a polymer formed by alcohol and phosphoric acid molecules, usually existing in the form of sugar ester or amino acid ester). The peptidoglycan layer is dense, even as many as 20 layers. However, the cell wall of gram-negative bacteria is much thinner than that of gram-positive bacteria, and the structure is more complex, divided into outer membrane and peptidoglycan layer (usually 2 nm to 3 nm).

The peptidoglycan layer is a unique component of the bacterial cell wall and is a derivative of heteropolysaccharide. Each peptidoglycan monomer comprises 3 portions: the sugar unit (for example, at least two sugar molecules are connected by glycosidic bond(s) to form the framework of peptidoglycan), the peptide tail (a short peptide chain formed by linking several amino acids, which is connected to a N-acetylmuramic acid molecule), and the peptide bridge (crosslinking adjacent "peptide tails" to form a high-strength network structure). Different bacteria have different peptide bridges, peptide tails and cross-linking manners.

Isolated *Rhodococcus ruber* Cell Wall Skeleton

In the present disclosure, "isolated *Rhodococcus ruber* cell wall" can be interpreted as either a complete cell wall or an incomplete cell wall (for example, disrupted or partially degraded). Under the teaching of the present disclosure, the skilled person will understand that the ingredients exhibiting the desired activity are derived from *Rhodococcus ruber* cell wall (for example, the cell wall itself or components thereof). Therefore, complete cell wall, disrupted cell wall, incomplete degradation product of cell wall, cell wall components, cell wall extracts and other various forms are allowed to be used in clinical applications, which are all encompassed in the scope of the present disclosure.

Cell Wall Skeleton

A component that constitutes the main structure of the cell wall; however, it cannot be interpreted as merely representing the cross-linked network-like entity in the cell wall, and the skilled person understands that other cell wall components adsorbed onto, bound to and carried by the cross-linked network-like entity are not excluded.

Rhodococcus ruber

The Rhodococcus ruber used in the embodiments of the present disclosure refers to the Rhodococcus ruber species of the Rhodococcus genus, and is not limited to a particular cell strain.

Non-limiting examples include the TOY7 strain (Agricultural Environment Microbiological Culture Collection, Nanjing Agricultural University), CGMCC No. 4795, DSM43338, CCTCC No. 2012035, CGMCC No. 16640 and CGMCC No. 17431.

Identification of Rhodococcus ruber

According to known or future microbial identification techniques, the skilled person can perform taxonomic identification on a strain of bacteria. For example, the available identification techniques include morphology, physiological and biochemical characteristics, 16S rRNA, and the like. The skilled person understands that with the development of science and technology, identification techniques involve different methods. In the earlier period, morphological and biochemical identification methods were mainly used, but the reliability of these methods is not high. After the advent of sequencing technology, the skilled person can identify bacteria strains in a more reliable way. For example, when the DNA sequences of 16S rRNA are identified as having more than 97% (inclusive) of identity, the two bacteria would be deemed as belonging to the same species (Hua Gougen et al., The taxonomy and application of Rhodococcus, Microbiology China, 2003:30(4)). In terms of Rhodococcus ruber, the known strains deposited in international (or national) collection authorities of strains are used as model strains, and the strains to be identified are compared with the model strains.

Dosage Form

The medicament or pharmaceutical composition or active ingredient or product of the present disclosure can be formulated into, but not limited to, the following forms: ointment, cream, plaster, gel, tablet, lotion, tincture, liniment, oil, paste, pulvis, powder, spray, aerosol, suppository, patch, suspension, oral rinse, buccal tablet, dressing, patch, bandage, film and gauze.

Formulation Unit

The medicament or pharmaceutical composition or active ingredient or product of the present disclosure can be formulated into the form of a formulation unit (or unit dose).

In some embodiments, the unit dose of the medicament (or formulation, or therapeutic agent, or medical device) comprises:

1 µg to 1000 µg of the product derived from Rhodococcus ruber; or
1 µg to 1000 µg of the Rhodococcus ruber cell wall; or
1 µg to 1000 µg of the Rhodococcus ruber cell wall skeleton.

Particular examples of the unit dose are 1, 2, 5, 10, 15, 20, 25, 30, 40, 50, 55, 56, 57, 58, 59, 60, 61, 62, 63, 65, 66, 67, 68, 69, 70, 80, 90, 100, 150, 200, 250, 300, 350, 400, 450, 500 µg±10%, and the ranges between any two of the above values.

"Administering", "dosing", "providing . . . to/with" and "treating", when applied to animals, humans, cells, tissues, organs or biological samples, refer to the contact of the medicament or medical device with the animals, humans, cells, tissues, organs or biological samples.

"Treatment" means administering an internal or external medicament (therapeutic agent, active ingredient or composition) (such as the Rhodococcus ruber cell wall or pharmaceutical composition thereof according to the present disclosure) or a medical device to a subject, in order to alleviate (relieve, delay, improve, cure) one or more disease symptom(s) to a clinically measurable degree in the subject (or population) to be treated, wherein the subject has, is suspected of having, or is susceptible to one or more diseases or symptom(s) thereof.

The amount of the medicament (therapeutic agent, active ingredient or composition) that can effectively alleviate any disease symptom is referred to as therapeutically effective amount. The therapeutically effective amount can vary depending on a variety of factors, such as the disease state, age and body weight of the subject. It should be understood that the medicament (therapeutic agent, active ingredient or composition) may be ineffective in alleviating the target disease or symptom thereof in a single subject, but is statistically effective for the target disease or symptom thereof according to any statistical test method known in the art (such as Student t test, chi-square test and U test according to Mann and Whitney).

"Optionally" means that the event following this term can happen, but not necessarily happen; it depends on the situation. For example, "optionally, performing aliquoting" means that the product is allowed to be aliquoted, but is not necessary to be aliquoted; whether the product is aliquoted or not does not affect the realization of the technical effects.

"A", "an", "single" and "the", if not explicitly stated, also involve plural forms.

The present disclosure is further described below with reference to the examples, preparation examples and test examples. However, these examples, preparation examples and test examples do not limit the scope of the present disclosure. When the particular conditions are not specified, operation should be performed in accordance with the normal conditions and the conditions recommended by the raw material supplier. The reagents without giving specific sources are conventional reagents purchased on the market.

The skilled person especially understands that although a specific cell strain is used in the following specific examples, the realization of the technical effects does not depend on the particular cell strain, and any species belonging to the Rhodococcus genus, Rhodococcus ruber species is applicable.

EXAMPLES

Example 1. Deposition of the Strain

The inventors deposited the laboratory-preserved seed strain at China General Microbiological Culture Collection Center, Yard No. 1(3) West Beichen Road, Chaoyang District, Beijing, on Mar. 22, 2019, under deposit number CGMCC No. 17431. Tests showed that the deposited strain was viable.

Example 2. Identification of the Strain

1. Visual Observation of the Morphological Characteristics of the Colonies

The strain was cultured on a glycerol agar medium at 30° C. to 37° C. (in particular 32° C. to 35° C.) for 12 to 72 (in particular 36 to 60, for example 40 to 50) hours, and the following was observed (FIG. 1):
- the colonies plumped up;
- were orange-red in color (slightly different depending on influences of light, the color of the culture medium, etc.);
- the surface was dry and wrinkled, slightly shiny (slightly different depending on differences in culture conditions);
- were fragile to the touch;
- the colony size was about 1 mm to 2 mm (slightly different depending on differences in culture conditions).

2. Microscope Observation

The bacteria grew in a branching structure with septate, and formed mycelium (slightly different depending on differences in culture conditions);

Division of the hyphae formed regular short and thick cells (slightly different depending on differences in culture conditions);

After culturing for 4 to 5 days, the bacteria became short rod-shaped or spherical (slightly different depending on differences in culture conditions).

3. Staining Property

The strain was gram stain positive.

4. Biochemical Reactions

The strain was cultured on a glycerol agar slant medium at 30° C. to 37° C. (in particular 32° C. to 35° C.) for 12 to 72 (in particular 36 to 60, for example 40 to 50) hours. Then, the following tests were performed on the culture.

4.1 Acid Production from Carbohydrates:
   Positive: Glycerin, mannitol, sorbitol, D-arabitol, D-fructose and D-glucose;
   Negative: Inositol, inulin, lactose, sucrose, starch, maltose, glycogen, xylitol, gluconate, trehalose, erythritol, melezitose, melibiose, raffinose, cellobiose, amygdalin, gentiobiose, adonol, arbutin, D-arabinose, L-arabinose, α-methyl-D-glucoside, α-methyl-D-mannoside, D-ribose, D-xylose, L-xylose, N-acetyl-glucosamine, D-turbiose, D-lyxose, β-methyl-D-xyloside, D-galactose, D-tagatose, D-fucose, L-fucose, D-mannose, L-sorbose, L-arabinitol, L-rhamnose and 2-keto-gluconate.

4.2 Enzyme Activity Determination (API ZYM):
   Positive: Alkaline phosphatase, lipid esterase (C8), lipase (C14), leucine araminase, valine araminase, cystine araminase, trypsin, chymotrypsin, acid phosphatase, naphthol-AS-B1-phosphohydrolase and α-glucosidase;
   Negative: N-acetyl-glucosaminidase, esterase (C4), β-galactosidase, β-uronidase, β-glucosidase, α-galactosidase, α-mannosidase and β-fucosidase.

4.3 Nitrate Reduction Reaction: Positive, Catalase: Positive, Tyrosinase:
   positive, amylase: negative, oxidase:
   negative, gelatin liquefaction: negative.

4.4 The Sole Carbon Source:
   Biolog Gen II Positive for: glucuronamide, β-hydroxy-DL growth butyric acid, D-fructose-6-phosphate, experiment: α-D-glucose, D-fructose, D-mannitol, D-arabitol, D-sorbitol, quinic acid, γ-aminobutyric acid, citric acid, L-malic acid, bromosuccinic acid, Tween 40, propionic acid and acetic acid;
   Biolog Gen III Sensitive to: dimethylamine tetracycline, chemical sodium tetradecyl sulfate, rifamycin SV, pH sensitivity 5.0, 8% sodium chloride, lincomycin, fusidic experiment: acid, D-serine, vancomycin, tetrazolium violet and tetrazolium blue;
   Tolerate to: sodium bromate, 1% sodium lactate, pH 6.0, 1%-4% sodium chloride, nalidixic acid, lithium chloride, potassium tellurite, aztreonam and sodium butyrate.

4.5. 16S rRNA Identification

The 15 strains isolated from the working seed tube and the 10 different strains isolated from the original seed tube were subjected to genome extraction, 16S rRNA amplification and sequencing. The 16S rRNA gene identity of the 25 strains in total was 100%. This means that the 25 strains were of the same species (FIG. 2).

Further, the neighbor-joining strain phylogenetic tree constructed based on the Kimura2-parameter algorithm showed that the strain was classified as *Rhodococcus ruber*.

Preparation Examples

Preparation Example 1. Culture Methods

1. *Rhodococcus ruber* can be cultured by conventional microbial production methods.
2. The culture method can be solid culture or liquid culture (for example flask or fermenter).
3. There are no special limitations on the nutrient sources in the culture medium. The culture medium contains carbon sources, nitrogen sources and other nutrient sources that are commonly used for culturing gram-positive bacteria.
   The carbon source can be any carbon source that can be consumed by *Rhodococcus ruber*. For example, fructose, glucose, etc.
   The nitrogen source: broth, peptone, ammonium salt, nitrate and other organic or inorganic nitrogen-containing compounds.
   Other nutrient sources: some inorganic salts can be added appropriately, for example, NaCl, phosphates, etc.
4. There are no strict limitations on the culture conditions (temperature, time, etc.). Those skilled in the art can choose the conditions that maximize the yield based on the preliminary small-scale pilot test data.
5. As an example, the following culture conditions was used to ferment *Rhodococcus ruber:*
   (1) The culture medium composition comprising:
   peptone, broth, sodium chloride, phosphate, glycerin (and, optionally, agar, when in solid culture).
   (2) Parameters of the culture method:
   After the working strain was recovered, it was transferred to a solid culture medium for 3 to 5 days, and then transferred to liquid culture (30° C. to 37° C., maintained for 3 to 5 days). The fed-batch semi-continuous mode or the batch mode can be used. The pH, bacterial density, dissolved oxygen and carbon source consumption were monitored during culture.

Preparation Example 2. Bacteria Disruption

The bacteria obtained in Preparation Example 1 were collected and the cells were disrupted (for example, but not limited to by sonication). Any appropriate well-known method in the art were also allowed to disrupt the bacteria, for example CN101250490A or CN101323865A.

The disruption state was checked under a microscope. There should be no more than 5 intact bacteria in each visual field. The disruption was deemed as qualified when several (10 to 30) visual fields checked met this standard.

Preparation Example 3. Removal of Non-Cell Wall Components

1. Removal of Nucleic Acids:

The product obtained after disruption was centrifuged. DNase and RNase were added to the obtained precipitate, and nucleic acids were removed according to the operation recommended by the supplier of the enzymes.

2. Removal of Proteins:

Commonly used protease (such as trypsin) was added to the precipitate, and proteins were removed according to the operation recommended by the supplier of the enzyme.

3. Removal of Lipids:

Organic reagents (for example, but not limited to, any one of acetone, ether and ethanol or a combination thereof) were added to the precipitate, and lipids were removed according to conventional operations in the art.

4. Removal of Cell Membranes:

Triton X-100 was added to the precipitate, and the precipitate was collected by centrifugation according to conventional operations in the art, and rinsed with PBS.

It should be understood that among the above steps for removing impurities, those skilled in the art can adjust the order of the steps to make them compatible with each other. After removing the non-cell wall components, the precipitate was re-constituted in water for injection, and then set aside till use. Optionally, it could be sterilized at 115° C. for 20 to 30 minutes as the stock solution of the cell wall skeleton (mainly comprising the cell wall skeleton and components thereof).

In addition to the above methods, the skilled person can also use known or future methods in the art to remove non-cell wall components, for example the method for extracting cell wall components disclosed in CN105779326A.

5. Yield

A total of 653 ml of bacterial liquid (after disruption) was collected from 159 Kolle flasks. The wet weight yield was 138 g; the cell wall skeleton yield was about 0.87 g/Kolle flask.

Preparation Example 4. Preparation Method of the Pharmaceutical Compositions (Medical Devices)

1. Liquid Composition

An excipient (such as dextran 40, mannitol or trehalose) was added to the product obtained in Preparation Example 3. The resulting product was referred to as the pharmaceutical composition after aliquoting.

TABLE 1

The pharmaceutical composition can be formulated in various forms

| Composition | Capacity of each vial | Components and amount | |
|---|---|---|---|
| Composition 1 | 2 ml | Active ingredient | 5 μg |
| | | Dextran 40 | 15 mg |
| Composition 2 | 2 ml | Active ingredient | 10 μg |
| | | Dextran 40 | 12 mg |
| Composition 3 | 2 ml | Active ingredient | 60 μg |
| | | Dextran 40 | 15 mg |
| Composition 4 | 2 ml | Active ingredient | 120 μg |
| | | Trehalose | 12 mg |
| Composition 5 | 2 ml | Active ingredient | 600 μg |
| | | Trehalose | 36 mg |
| Composition 6 | 2 ml | Active ingredient | 100 μg |
| | | Mannitol | 12 mg |
| Composition 7 | 2 ml | Active ingredient | 800 μg |
| | | Mannitol | 36 mg |

2. Lyophilized Composition

The pharmaceutical compositions of item 1 were lyophilized to prepare lyophilized powders (numbered as lyophilized compositions 1 to 7, respectively).

3. Preparation Method of the Formulations (1) Dressing

The pharmaceutical composition of item 1 (active ingredient 60 μg to 120 μg, for example 60 μg, 70 μg, 80 μg, 90 μg, 100 μg, 110 μg, 120 μg) was coated on dressings (for example sterile gauzes) to prepare a medical device for external use.

(2) Patch or Film

The film is prepared by using well-known methods in the art (for example methods disclosed in Chinese Application No. 201610605617.5, 201510614414.8, 200610200450.0, 201610511974.5, 201610471977.0, etc.).

For example: film-forming materials (polyvinyl alcohol, carbomer and hydroxypropyl cellulose) were added into water for swelling and forming a homogeneous viscous liquid; the pharmaceutical compositions of item 1 (compositions 1 to 7, respectively) were added into the viscous liquid and mixed well; the mixture was let stand to defoam; a mixed viscous liquid without bubbles was formed and casted onto a mold which was coated with a small amount of paraffin, and were dried for 5 to 20 min, and the film was taken out and cut into the required size.

(3) Gel

The composition can also be formulated into a gel form. For example, referring to the method disclosed in Chinese Application No. 200510028076.6, the composition 3 and the esterification agent were stirred and dissolved in a solvent, hydroxyalkyl cellulose was added for swelling, and stirred continuously to form a gel; then a crosslinking agent was added and stirred continuously until the gel was completely homogeneous.

(4) Ointment

The preparation method of ointment for external use on skin can also be found in, but not limited to the methods disclosed in Chinese Application No. 201610856428.5, 01133296.4, 1133297.2 and "Dosage Form and Formulation Design" (Chemical Industry Press 2009).

4. Quality Inspection (Lyophilized Composition 3 was Taken as an Example)

TABLE 2

| Quality inspection items | |
|---|---|
| Appearance | White unconsolidated solid or powder |
| Water content | ≤6% |
| Solubility | The product was deemed as qualified if it dissolved within 1 min when 2.0 ml of NaCl injection was added; |
| Identification of saccharides | The solution was blue-green in color |
| Content of muramic acid | 2.0 μg/vial (criteria: ≥1.0 μg/vial) |
| Residual amount of proteins | 0.4 μg/vial (criteria: ≤9.0 μg/vial) |
| Residual amount of RNA | 0.8% (criteria: not more than 5%) |
| Residual amount of DNA | 0.9% (criteria: not more than 5%) |
| Residual amount of Triton X-100 | Undetectable (criteria: not more than 5%) |
| Residual amount of lipids | 3.8% (criteria: not more than 5%) |
| Phagocytosis rate | 75% (criteria: ≥40%) |
| Phagocytic index | 1.05 (criteria: ≥0.50) |
| Abnormal toxicity in mice | All the mice should survive and have no abnormal reactions during the observation period. The composition was deemed as qualified if the body weight of each mouse increased at the due date |
| Abnormal toxicity in guinea pigs | All the guinea pigs should survive and have no abnormal reactions during the observation period. The composition was deemed as qualified if the body weight of each guinea pig increased at the due date |

Test Example

1. Materials
1.1 Drugs and Main Reagents
   Test drug: lyophilized composition 3 obtained in the aforementioned Preparation Examples (60 μg active ingredient/vial);
   Control drug: Ching Wan Hung ointment (Tianjin Darentang Jingwanhong Pharmaceutical Co., Ltd., medicine permission No. Z20023137, specification 30 g/tube);
   Veet Hair Removal Cream (Reckitt Benckiser (China) Co., Ltd.);
   Ether (Sinopharm Chemical Reagent Co., Ltd.).
1.2 Experimental Animals
   16 clean-grade Kunming mice, weighing 28 g to 36 g, were provided by Liaoning Changsheng Biotechnology Co., Ltd., with certificate number 211002300051326.
2. Experimental Methods
2.1 Experimental Design
   16 Kunming mice were randomly divided into 4 groups, with 4 in each group:
   1) Model group;
   2) Unbroken wound treatment group (*Rhodococcus ruber* group);
   3) Broken wound treatment group (*Rhodococcus ruber* group);
   4) Positive control group (control drug).
2.2 Preparation of Second Degree Scald Mouse Model
   The mice were adapted to the environment and kept for one week. After shaving the skin on the back of mice with a shaver, a depilatory cream was used to remove the hair (in an area of about 3.5 cm×3.5 cm) and let stand for 180 s. The depilated area was washed with warm water at 30° C. to 40° C. and wiped dry with degreasingcotton.
   After depilation, the mice were kept normally for 24 h and observed, confirming that there were no abnormal conditions such as redness, inflammation and broken skin at the depilated site. After 24 h, the mice were anesthetized with ether, placed on an operating table, the skin in the experimental area was disinfected with 75% ethanol, and the scald model was constructed.
   The mice were placed on the device for scalds with a 1.5 cm hole in the middle, making the depilated skin on the back be at the place of the hole. The 1.5 cm hole with the back exposed was kept in water at a constant temperature of 75° C. for 12 s, thus making a round-shaped scald wound with a diameter of about 1.5 cm.
   The injured mice were kept in separate cages, the wounds were treated with saline, feed and distilled water were given, and the bedding was ensured to be dry and clean, with good ventilation. According to the Rule of three degrees with four levels, the burn/scald was identified as deep second grade.
2.3 Grouping and Administration
   Administration started 24 h after the scald:
   Model group: physiological saline was applied to the scald wound on the skin of each mouse every day;
   Unbroken wound treatment group: the wound was first treated with physiological saline, and then composition 3 was externally applied to every animal every day (1 vial; 0.25 ml of physiological saline was injected into the vial to completely dissolve the lyophilized powder, which was used to completely impregnate 3 layers of 1.2 cm×1.2 cm gauze for application on the wound, and then fixed with medical desensitization tape);
   Broken wound treatment group: the wound was first treated with physiological saline and made broken, and then composition 3 was externally applied to every animal every day (1 vial; 0.25 ml of physiological saline was injected into the vial to completely dissolve the lyophilized powder, which was used to completely impregnate 3 layers of 1.2 cm×1.2 cm gauze for application on the wound, and then fixed with medical desensitization tape);
   Positive control group: the wound was first treated with physiological saline, and then Ching Wan Hung ointment was externally applied to every animal once every day.
   The wound healing was observed on Day 1, 3, 7, 11 and 15 of the administration.

3. Experimental Observation and Index Detection 3.1 Determination of Wound Healing Time For each group, the healing time was determined. The determination criteria include:

Healed: the scabs completely fell off at the scald site, and the surface of the repaired tissue was fresh and relatively flat;

Basically healed: the scabs intermittently fell off, the surface of the newly growntissue was not very flat, with a small amount of exudate in a small area but no obvious infection focus;

Infected: obvious redness and swelling appeared around the scabs, with pus or ulcer under the scab.

3.2 Wound Healing Rate

The wound healing of mice was observed and recorded on Day 3, 7, 11 and 15 of the administration. Complete epithelialization and no exudation of the wound were regarded as complete healing of the wound. At the same time, the wound was observed for redness, swelling, infection, etc. The wound healing rate at each time point was calculated: the diameter of the wound was obtained according to the scale in the photo and by graphic processing softwares, and the wound area was calculated.

Wound healing rate %=(original wound area−unhealed wound area)/original wound area×100%.

3.3 Statistical Methods

SPSS 17.0 statistical software was used for analysis, and one-way ANOVA was used for comparison between groups. The data obtained was represented as $\bar{x}\pm s$. $P<0.05$ was considered statistically significant.

4. Experimental Results 4.1 General Observations

All mice survived until the wounds healed, and there were no obvious differences in eating, drinking, mental state, activity, etc., and no obvious signs of infection.

4.2 Wound Healing 4.2.1 Wound Healing Time

Complete healing of the wounds and a relatively flat tissue surface of mice were considered as the standard for healing Compared with the model group, the wound healing time of the broken wound treatment group and the positive group was shortened, and the difference was statistically significant $P<0.05$. Compared with the positive group, the healing time of the broken wound treatment group was slightly earlier than that of the positive group, and the difference was statistically significant $P<0.05$.

TABLE 3

Wound healing time of deep second degree scald in mice ($\bar{x}\pm s$)

| Group | n | Wound healing time/d |
|---|---|---|
| Model group | 4 | 22.3 ± 0.4 |
| Unbroken wound treatment group | 4 | 21.4 ± 0.3 |
| Broken wound treatment group | 4 | 15.9 ± 0.3* |
| Positive group | 4 | 17.3 ± 0.4* |

Note: compared with model group, *$P<0.05$ 4.2.2 Wound Healing Rate

Administration started 24 h after the model was established. The wound area before administration was set as the reference area. The wound area on Day 3, 7, 11 and 15 was recorded, and the healing rate was calculated.

Compared with the model group, the wound healing rate of the broken wound treatment group started to be significantly higher than that of the model group at Day 7 of administration, and the healing rate of the positive group and the unbroken wound treatment group also started to be higher than that of the model group at Day 11 of administration, with statistical significance $P<0.05$. Compared with the positive group, the wound healing rate of the broken wound treatment group started to be higher than that of the positive group at Day 7 of administration, and with statistical significance $P<0.05$.

TABLE 4

Wound healing rate of deep second degree scald in mice ($\bar{x}\pm s$)

| Group | n | 3 d | 7 d | 11 d | 15 d |
|---|---|---|---|---|---|
| Model group | 4 | 13.21 ± 1.82 | 32.38 ± 6.96 | 58.45 ± 8.21 | 82.08 ± 6.48 |
| Unbroken wound treatment group | 4 | 11.92 ± 6.22 | 32.18 ± 13.97 | 66.31 ± 4.35* | 89.05 ± 1.53* |
| Broken wound treatment group | 4 | 13.98 ± 4.61 | 38.77 ± 2.95* | 76.46 ± 4.05* | 97.85 ± 0.16* |
| Positive group | 4 | 12.47 ± 3.72 | 32.13 ± 6.28 | 67.63 ± 14.76* | 91.86 ± 1.98* |

Note: compared with model group, *$P<0.05$

4.2.3 Wound Healing State

When the broken wound treatment group healed, the wound had no scar hyperplasia and was smooth, while other groups showed different degrees of scar hyperplasia; meanwhile, the wound site of the broken wound treatment group started to grow hair.

In summary, during the healing process of deep second degree scalds in mice, the *Rhodococcus ruber* cell wall skeleton can effectively improve the healing rate, shorten the healing time, reduce the formation of scars after wound healing, while having a significant repairing effect on hair follicles and other appendages of the skin.

What is claimed is:

1. A method of treating a thermal injury, including:
   administering to a subject in need thereof, a therapeutically effective amount of *Rhodococcus ruber* cell wall skeleton, wherein the *Rhodococcus ruber* cell wall skeleton is in a form selected from the group consisting of: ointment, cream, emulsion, suspension, paste, gel, lotion, tincture, oil, tablet, aerosol, spray, liniment, powder, dressing, bandage, film, patch and suppository; wherein
   the *Rhodococcus ruber* is the isolated *Rhodococcus ruber* deposited in CGMCC under Accession No: 17431;
   the unit dosage of the *Rhodococcus ruber* cell wall skeleton is 5 μg to 800 μg;
   wherein the *Rhodococcus ruber* cell wall skeleton is obtained by the following method comprising the following steps:
   1) providing a *Rhodococcus ruber*;
   2) disrupting the *Rhodococcus ruber* to obtain a disrupted product;
   3.1) optionally, removing lipids from the disrupted product;
   3.2) optionally, removing nucleic acids from the disrupted product;
   3.3) optionally, removing proteins from the disrupted product;
   3.4) obtaining a product derived from *Rhodococcus ruber* cell wall;
   4) optionally, removing water from the product derived from *Rhodococcus ruber* cell wall;
   5) optionally, performing aliquoting;
   wherein, steps 3.1), 3.2) and 3.3) are interchangeable in order or performed in parallel; step 4) and step 5) are interchangeable in order; and
   the average particle size of the disruption is 10 nm to 1000 nm.

2. The method of claim 1, wherein the therapeutically effective amount of *Rhodococcus ruber* cell wall skeleton is administered to the subject twice a day, once a day, once every two days, three times every two days, once every three days, or once a week.

3. The method of claim 1, wherein administration provides contact of the therapeutically effective amount of *Rhodococcus ruber* cell wall skeleton with the subject for 30 minutes to 24 hours each administration.

4. The method of claim 1, wherein administration provides contact of the therapeutically effective amount of *Rhodococcus ruber* cell wall skeleton with the subject for 2 days or longer.

5. The method of claim 1, wherein the thermal injury is selected from the group consisting of: burn, scald and chemical burn.

6. The method of claim 5, wherein the thermal injury involves one or more tissues selected from the group consisting of: epidermis, dermis, mucosa and subcutaneous tissue.

7. The method of claim 5, wherein the thermal injury is selected from the group consisting of: first degree, second degree, and third degree.

8. The method of claim 1, wherein—in step 4), removing water from the product derived from *Rhodococcus ruber* cell wall by lyophilization.

9. The method of claim 8, wherein aliquoting is into one or more containers; on to one or more solid supports; or both.

10. The method of claim 9, wherein the container is selected from the group consisting of: vial, tube, package, bag, plate, ampoule, injection device, aluminum-plastic packaging, dressing and capsule.

11. The method of claim 5, wherein the thermal injury is deep second degree.

12. A method of preparing a medicament for the treatment of thermal injury, the method comprising providing *Rhodococcus ruber* cell wall skeleton, wherein the medicament is for the treatment of thermal injury; and
   formulating a medicament comprising the *Rhodococcus ruber* cell wall skeleton into a dosage form selected from the group consisting of: ointment, cream, emulsion, suspension, paste, gel, lotion, tincture, oil, tablet, aerosol, spray, liniment, powder, dressing, bandage, film, patch and suppository, wherein the medicament comprises 1 μg to 1000 μg/unit dose of *Rhodococcus ruber* cell wall skeleton;
   the *Rhodococcus ruber* is the isolated *Rhodococcus ruber* deposited in CGMCC under Accession No: 17431;
   wherein the *Rhodococcus ruber* cell wall skeleton is obtained by the following method comprising the following steps:
   1) providing a *Rhodococcus ruber*;
   2) disrupting the *Rhodococcus ruber* to obtain a disrupted product;
   3.1) optionally, removing lipids from the disrupted product;
   3.2) optionally, removing nucleic acids from the disrupted product;
   3.3) optionally, removing proteins from the disrupted product;
   3.4) obtaining a product derived from *Rhodococcus ruber* cell wall;
   4) optionally, removing water from the product derived from *Rhodococcus ruber* cell wall;
   5) optionally, performing aliquoting;
   wherein, steps 3.1), 3.2), and 3.3) are interchangeable in order or performed in parallel; and step 4) and step 5) are interchangeable in order.

13. The method of claim 12, wherein the thermal injury is selected from the group consisting of: burn, scald and chemical burn and involves one or more tissues selected from the group consisting of: epidermis, dermis, mucosa and subcutaneous tissue.

14. The method of claim 13, wherein the medicament comprises 5 μg to 800 μg/unit dose of *Rhodococcus ruber* cell wall skeleton.

15. The method of claim 12, wherein the thermal injury is deep second degree.

16. The method of claim 12, wherein the medicament further comprises a pharmaceutically acceptable excipient and the *Rhodococcus ruber* cell wall skeleton is 1 part by weight, and the pharmaceutically acceptable excipient is 100 to 1000 parts by weight.

17. The method of claim 15, wherein the *Rhodococcus ruber* cell wall skeleton is 1 part by weight, and the pharmaceutically acceptable excipient is 250 parts by weight and the medicament is a liquid, a powder formulation, or a lyophilized formulation.

18. The method of claim 12, wherein the average particle size of the disruption is 10 nm to 1000 nm.

19. The method of claim 12, wherein the aliquoting refers to aliquoting into one or more container, onto one or more solid support, or both; and the container is selected from the group consisting of: vial, tube, package, bag, plate, ampoule, injection device, aluminum-plastic packaging, dressing and capsule.

* * * * *

SEQUENCE LISTING

<160> NUMBER OF SEQ ID NOS: 1

<210> SEQ ID NO 1
<211> LENGTH: 1364
<212> TYPE: DNA
<213> ORGANISM: Rhodococcus ruber

<400> SEQUENCE: 1

```
ggttaggcca ccggcttcgg gtgttaccga ctttcatgac gtgacgggcg gtgtgtacaa    60
ggcccgggaa cgtattcacc gcagcgttgc tgatctgcga ttactagcga ctccgacttc   120
acggggtcga gttgcagacc ccgatccgaa ctgagaccgg ctttaaggga ttcgctccac   180
ctcgcggtat cgcagccctc tgtaccggcc attgtagcat gtgtgaagcc ctggacataa   240
ggggcatgat gacttgacgt cgtccccacc ttcctccgag ttgaccccgg cagtctcctg   300
cgagtcccca ccattacgtg ctggcaacac aggacaaggg ttgcgctcgt tgcgggactt   360
aacccaacat ctcacgacac gagctgacga cagccatgca ccacctgtac accgaccaca   420
agggaaaccc catctctggg gcggtccggt gtatgtcaaa cccaggtaag gttcttcgcg   480
ttgcatcgaa ttaatccaca tgctccgccg cttgtgcggg ccccgtcaa ttcctttgag    540 ttttagcctt gcggccgtac tccccaggcg gggcgcttaa tgcgttagct acggcacgga   600
tcccgtggaa ggaaacccac acctagcgcc caccgtttac ggcgtggact accagggtat   660
ctaatcctgt tcgctaccca cgctttcgct cctcagcgtc agttactgcc cagagacccg   720
ccttcgccac cggtgttcct cctgatatct gcgcatttca ccgctacacc aggaattcca   780
gtctcccctg cagtactcaa gtctgcccgt atcgcctgca agcccgcagt tgagctgcgg   840
gttttcacag acgacgcgac aaaccgccta cagctcttta cgcccagtaa ttccggacaa   900
cgctcgcacc ctacgtatta ccgcggctgc tggcacgtag ttggccggtg cttcttctgt   960
acctaccgtc acttgcgctt cgtcggtact gaaagaggtt tacaacccga aggccgtcat  1020
ccctcacgcg gcgtcgctgc atcaggcttg cgcccattgt gcaatattcc ccactgctgc  1080
ctcccgtagg agtctgggcc gtgtctcagt cccagtgtgg ccggtcgccc tctcaggccg  1140
gctacccgtc gtcgccttgg tgggccgtta ccccaccaac aagctgatag gccgcgggcc  1200
catcctgcac cggaaaacct ttccaccccg aacatgcatc ccgaggtcct atccggtatt  1260
agacccagtt tccaggcttt atcccgaagt gcagggcaga tcacccacgt gttactcacc  1320
cgttcgccac taatccaccc agcaagctgg cttcatcgtt cgac                    1364
```